United States Patent
Stephens et al.

(10) Patent No.: US 10,125,336 B2
(45) Date of Patent: *Nov. 13, 2018

(54) LUBRICATING SHAVING AID MEMBER

(71) Applicant: The Gillette Company, Boston, MA (US)

(72) Inventors: Alison Fiona Stephens, Maidenhead (GB); Neil John Jones, Staines (GB); Valerie Jean Bradford, Framingham, MA (US); Elaine Alice Marie Baxter, St. Margarets (GB)

(73) Assignee: The Gillette Company LLC, Boston, MA (US)

( * ) Notice: Subject to any disclaimer, the term of this patent is extended or adjusted under 35 U.S.C. 154(b) by 111 days.

This patent is subject to a terminal disclaimer.

(21) Appl. No.: 14/259,238

(22) Filed: Apr. 23, 2014

(65) Prior Publication Data

US 2014/0323374 A1 Oct. 30, 2014

Related U.S. Application Data

(60) Provisional application No. 61/815,459, filed on Apr. 24, 2013.

(51) Int. Cl.
F16C 33/20 (2006.01)
C10M 107/34 (2006.01)
A61Q 9/02 (2006.01)
A61K 8/86 (2006.01)
A61K 8/90 (2006.01)
B26B 21/44 (2006.01)

(52) U.S. Cl.
CPC ............. *C10M 107/34* (2013.01); *A61K 8/86* (2013.01); *A61K 8/90* (2013.01); *A61Q 9/02* (2013.01); *A61K 2800/87* (2013.01); *B26B 21/443* (2013.01); *C10M 2209/1045* (2013.01); *C10M 2209/1075* (2013.01)

(58) Field of Classification Search
CPC .. C10M 107/34; C10M 107/04; B26B 21/165
USPC .................................. 508/100, 579; 30/538
See application file for complete search history.

(56) References Cited

U.S. PATENT DOCUMENTS

| 5,134,775 A | 8/1992 | Althaus et al. |
| 5,454,164 A * | 10/1995 | Yin ...................... B26B 21/443 30/41 |
| 5,653,971 A | 8/1997 | Badin et al. |
| 5,711,076 A | 1/1998 | Yin et al. |
| 6,298,558 B1 | 10/2001 | Tseng et al. |
| 6,301,785 B1 | 10/2001 | Kwiecien et al. |

(Continued)

OTHER PUBLICATIONS

PCT International Search Report with Written Opinion in corresponding Int'l appln. PCT/US2014/034770 dated Jul. 22, 2014.

(Continued)

Primary Examiner — Prem C Singh
Assistant Examiner — Francis C Campanell
(74) Attorney, Agent, or Firm — Ronald T. Sia; Kevin C. Johnson

(57) ABSTRACT

A shaving aid member comprising a lubricating material, the lubricating material comprising a water soluble polymer having an average molecular weight of at least 5,000, and a copolymer of polyethylene oxide and polypropylene oxide.

10 Claims, 2 Drawing Sheets

(56) References Cited

U.S. PATENT DOCUMENTS

| | | | |
|---|---|---|---|
| 7,121,754 B2 | 10/2006 | Bressler et al. | |
| 2006/0225285 A1 | 10/2006 | Slavtcheff et al. | |
| 2009/0223057 A1 | 9/2009 | Coope-Epstein et al. | |
| 2012/0093897 A1* | 4/2012 | Stephens | A61K 8/31 424/401 |
| 2013/0042482 A1 | 2/2013 | Bradford et al. | |

OTHER PUBLICATIONS

Chemal Data from Alfa Chemicals Technical Brochure.
Pluronics Data from BASF Technical Brochure.

* cited by examiner

US 10,125,336 B2

LUBRICATING SHAVING AID MEMBER

FIELD OF THE INVENTION

The present invention concerns shaving aid members, especially those for use on hair removal cartridges or devices, the cartridges or devices themselves, and methods of making the same.

BACKGROUND OF THE INVENTION

The use of shaving aids on razor blades to provide lubrication benefits during the shave is known. See e.g., U.S. Pat. Nos. 7,121,754; 6,298,558; 5,711,076; 5,134,775; 6,301,785 and U.S. Patent Publ. Nos. 2009/0223057, 2006/0225285. Such shaving aids typically comprise a water-insoluble matrix material to provide structural integrity and a water-soluble polymer such as polyethylene oxide (polyox) in order to provide the lubrication during the shave once the water-soluble polymer enters solution with water present during shaving. Since the application of polyox as a shaving lubricant, little development has been made in the field, though polyox is not without its limitations. For example, the use of polyox with low molecular weight offers limited lubrication, and while improved lubrication may be seen when using polyox with higher molecular weights, this impacts other aspects of the aqueous solution typically formed in-use, for example the resultant viscosity in aqueous solution may also increase, leading to negatively perceived attributes, for example concerning the feeling of the shave for the user, particularly in respect of the lubricant. Accordingly, there remains a need for technologies that can break this paradigm in order to offer improved lubrication benefits, ideally without negative impact to consumer perception.

SUMMARY OF THE INVENTION

One aspect of this invention relates to a shaving aid member comprising a lubricating material, the lubricating material comprising a water soluble polymer having an average molecular weight of at least 5,000 and a copolymer of polyethylene oxide and polypropylene oxide. A further aspect of the invention relates to a razor cartridge comprising the aforementioned shaving aid member. Another aspect of the invention relates to a shaving device comprising the aforementioned shaving aid member. Another further aspect of the invention relates to a method of making a shaving aid member comprising the copolymer of polyethylene oxide and polypropylene oxide.

DETAILED DESCRIPTION OF THE INVENTION

I. Lubricating Material

Figure 1:
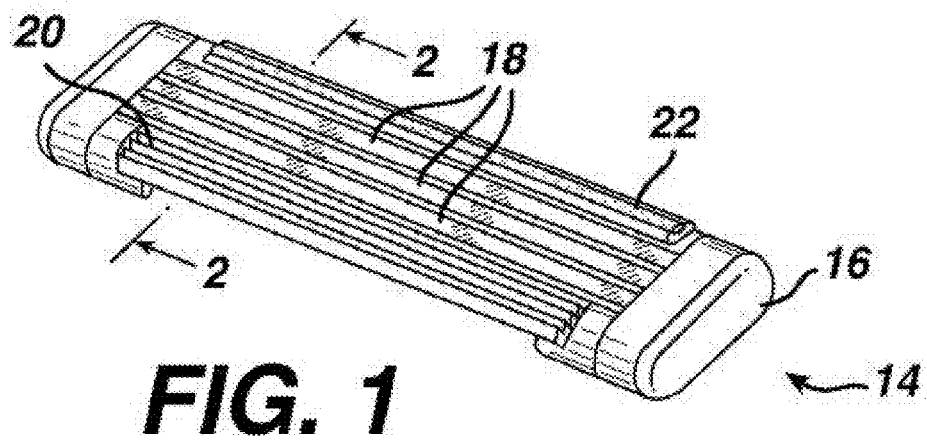
FIG. 1 is a perspective view of a razor cartridge which includes a shaving aid member of the present invention.

The shaving aid member (or skin-engaging shaving aid member) comprises a lubricant, or lubricating material, comprising a water soluble polymer typically intended to provide lubrication in-use and having an average molecular weight of at least 5000. The lubricating material can be in various forms, as well as mixtures/combinations thereof as will be described below.

Examples of water soluble polymers include polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and a mixtures thereof. In some embodiments, said water soluble polymer is selected from the group consisting of polyethylene oxide, polyethylene glycol, and mixtures thereof.

The water-soluble polymer will preferably comprise at least about 50%, more preferably at least about 60%, by weight of the shaving aid member, up to about 99%, (or up to about 90% of the lubricating material). For example, the water-soluble polymer may be present at an amount of at least about 50%, preferably from about 50% to about 99.9%, more preferably from about 60% to about 95% (e.g. from about 90% to about 95%) and even more preferably from about 70% to about 90% by weight of the lubricating material. Not all of the water-soluble polymer needs to meet the average molecular weight requirement, for example a blend of two or more grades of polyethylene oxide could be used wherein at least one, but less than all, of the grades meets the average molecular weight attribute, but the total amount of polyethylene oxide is within one of the ranges above. Alternatively, the average molecular weight for the entirety of the water-soluble polymer (especially polyethylene oxide) may fall within the desired average molecular weight range as well as the total amount of water-soluble polymer (especially polyethylene oxide) being according to one or more of the ranges above.

The more preferred water soluble polymers are the polyethylene oxides generally known as POLYOX (available from Union Carbide Corporation) or ALKOX (available from Meisei Chemical Works, Kyoto, Japan). The water soluble polymer, (especially these polyethylene oxides), will preferably have average molecular weights of at least about 20,000, at least about 50,000, at least about 100,000 or from about 100,000 to 6 million, preferably about 300,000 to 5 million. A particularly preferred polyethylene oxide comprises a blend of about 40% to 80% of polyethylene oxide having an average mol.wt. of about 5 million (e.g. POLYOX COAGULANT) and about 60% to 20% of polyethylene oxide having an average mol.wt. of about 300,000 (e.g. POLYOX WSR-N-750). The polyethylene oxide blend may also advantageously contain up to about 10% (for example about 5%) by weight of a low mol.wt. (i.e. MW<10,000) polyethylene glycol such as PEG-100.

II. Copolymer of Polyethylene Oxide and Polypropylene Oxide

The shaving aid member further comprises a copolymer of polyethylene oxide (PEO) and polypropylene oxide (PPO) to improve the lubrication properties of the shaving aid member. The PEO/PPO copolymer may have any average molecular weight. Advantageously, the PEO/PPO copolymer has an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the water soluble polymer in aqueous solution, especially for polyethylene oxide, and thus prevent an undesirable feeling in use.

The PEO/PPO copolymer may be of any arrangement but is advantageously a block copolymer, for example a di-block, tri-block, multi-block, radial-block or random-block copolymer. Preferably, the PEO/PPO copolymer is a tri-block copolymer, more preferably a tri-block copolymer having the sequence: PEO-PPO-PEO. Such tri-block copolymers of PEO and PPO are commercially available under trade names such as Pluracare from BASF and Pluronic from Sigma-Aldrich.

The PEO/PPO copolymer may have any weight ratio of PEO to PPO (i.e. of ethylene oxide repeat units to propylene oxide repeat units), for example anywhere from 1000:1 to 1:1000 or from 100:1 to 1:100. Advantageously, the weight ratio is selected to improve the solubility properties of the PEO/PPO copolymer in a system comprising a water-soluble polymer (especially polyethylene oxide) and water, and so may be from 10:1 to 1:10, preferably from 1:1 to 1:7 (or any ratio in which the weight of PPO is greater than or equal to the weight of PEO), more preferably from 1:2 to 1:5, even more preferably from 1:2.5 to 1:4 and even more preferably still from 1:2.5 to 1:3.

An alternative way of describing the solubility properties of the PEO/PPO copolymer is through the well known hydrophilic-lipophilic balance (HLB). The PEO/PPO copolymer may have an HLB of from 0 to 50, but advantageously will have an HLB in the range of from 1 to 30, preferably from 5-25, more preferably from 10-25, even more preferably from 17-24 and even more preferably still from 18-23.

The PEO/PPO copolymer is typically present at an amount of from 0.01% to 50% by weight of the lubricating material, or by weight of the shaving aid member. Preferably, the PEO/PPO copolymer is present at an amount of from 0.01% to 50%, preferably from 2% to 40%, more preferably from 3% to 25%, even more preferably from 4% to 20% and even more preferably still from 5% to 10% by weight of the lubricating material or by weight of the shaving aid member, in order to provide an improved balance between the water soluble polymer providing lubrication and the PEO/PPO copolymer to address the problems associated with the water soluble polymer.

III. Water Insoluble Polymer

The shaving aid member can further comprise a water-insoluble polymer, e.g. in which the water-soluble polymer is dispersed, which may be referred to as a water-insoluble matrix. Preferably, the water insoluble polymer is present at a level of from about 0% to about 50%, more preferably about 5% to about 40%, and even more preferably about 15% to about 35% by weight of the shaving aid member. Suitable water-insoluble polymers which can be used include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof such as polypropylene/polystyrene blend or polystyrene/impact polystyrene blend.

One preferred water-insoluble polymer is polystyrene, preferably a general purpose polystyrene, such as NOVA C2345A, or a high impact polystyrene (HIPS) (i.e. polystyrene-butadiene), such as BASF 495F KG21. The strip or any portion should contain a sufficient quantity of water-insoluble polymer to provide adequate mechanical strength, both during production and use. In some embodiments, the shaving aid member comprises any other ingredients commonly found in commercially available shaving aid members, such as those used on razor cartridges by Gillette, Schick or BIC. Non-limiting examples of such shaving aid members include those disclosed in U.S. Pat. Nos. 6,301,785, 6,442,839, 6,298,558, 6,302,785, and U.S Patent Pubs 2008/060201, and 2009/0223057.

IV. Further Optional Ingredients

The shaving aid member or lubricating material may contain other conventional shaving aid member ingredients, such as low mol.wt. water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, skin care actives, surfactants, soaps (including interrupted soaps), antioxidants, preservatives, emollients, lipids, oils, waxes, fats, cooling agents (especially non-volatile cooling agents), essential oils, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials etc.

Portions that contain a colorant can be designed to release the colorant (e.g., by leaching or abrasion), and thereby cause the strip to change color during shaving, preferably in response to wear of the colored portion, so as to provide an indication to the user that the shaving aid member and/or the razor cartridge has reached the end of its effective life or the end of its optimum performance. A portion may contain, for example, between about 0.1% and about 5.0% (preferably between about 0.5% and 3%) colorant by weight.

In some embodiments, the lubricating material further comprises from about 0.5% to about 50%, preferably from about 1% to about 20%, polycaprolactone (preferably mol.wt. of 30,000 to 60,000). See U.S. Pat. No. 6,302,785.

In some embodiments, the shaving aid member further comprises a shaving aid member ingredient, for example selected from the group consisting of polyvinyl pyrrolidone, polyacrylamide, hydroxypropyl cellulose, polyvinyl imidazoline, polyethylene glycol, poly vinyl alcohol, polyhydroxyethylmethacrylate, silicone copolymers, sucrose stearate, vitamin E, panthenol, aloe, polyethylene glycol, silicone oil, Teflon® polytetrafluoroethylene powders (manufactured by DuPont), menthol, camphor, eugenol, eucalyptol, safrol and methyl salicylate; tackifiers such as Hercules Regalrez 1094 and 1126, cyclodextrins, inclusion complexes of skin-soothing agents with cyclodextrins; antimicrobial/keratolytic materials such as Resorcinol; anti-inflammatory agents such as Candilla wax and glycyrrhetinic acid; astringents such as zinc sulfate; surfactants such as iconol materials; compatibilizers such as styrene-b-EO copolymers; mineral oil, polycaprolactone (PCL), and combinations thereof.

V. Carrier

In some embodiments, the shaving aid member further comprises a carrier wherein the lubricating material and if present any water-insoluble matrix and other materials can be contained within the carrier and/or present on the carrier. The carrier can be in the form of a tray upon which the lubricating material and if present any water-insoluble matrix or other materials are applied, or the carrier can form a retaining structure at least partially containing the lubricating material and if present any water-insoluble matrix or other materials. In some embodiments, the carrier forms a reservoir, for example from which shaving aid is dispensed to the skin with or without direct contact between the carrier and the skin, and such as the sheaths disclosed in U.S. Pat. Nos. 6,298,558 and 7,581,318. Especially where the lubricating material comprises a fluid or solid intended to be dissolved during shaving, but applicable generally, the carrier is preferably a sheath having one or more dispensing orifices to control the dispensing of one or more of the materials of the skin engaging member. When referring to the compositional make up of the shaving aid member, the weight percentages defined herein are determined based on the other components of the shaving aid member disclosed herein but not the carrier, unless otherwise specified.

VI. Razor Cartridge

According to some embodiments of the invention, a hair removal cartridge (e.g. a razor cartridge or shaving head) is provided, comprising a housing, at least one hair removal member within the housing and at least one shaving aid member according to the invention as described hereinabove.

The hair removal cartridge comprises one or more elongated edges or hair removal members (e.g. blades) usually positioned between a first and second end, said one or more elongated edges comprising a tip extending towards said first end. For example, U.S. Pat. No. 7,168,173 generally describes a Fusion® razor that is commercially available from The Gillette Company and which includes a razor cartridge with multiple blades. Additionally, the hair removal cartridge, or razor cartridge, may include a guard as well as a shaving aid member. A variety of razor cartridges can be used in accordance with the present invention. Nonlimiting examples of suitable razor cartridges, with and without fins, guards, and/or shave aids, include those marketed by The Gillette Company under the Fusion®, Venus® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the present shaving aid member can be used with any currently marketed system or disposable razor, including those having 2, 3, 4, 5 or more blades.

The elongated edge is the structure responsible for cutting, pulling or shearing off the hair from the skin. For example, the hair removal member may be one or more blades; a scraping edge which can be used after a depilatory is applied onto the skin to be treated or a plurality of tweezer members which can be used for epilation (pulling hairs out of the follicle).

In some embodiments, said at least one shaving aid member is located on the portion of the cartridge that contacts skin during the shaving process, forward, between, and/or aft of the hair removal member(s). A feature "forward" of the one or more hair removal members, for example, is positioned so that the surface to be treated with by the shaving device encounters the feature before it encounters the hair removal members. A feature "aft" of a hair removal member is positioned so that the surface to be treated by the shaving device encounters the feature after it encounters the hair removal member. Where more than one shaving aid member is provided on the shaving device, they can be the same (identical) or different, in terms of physical shape/structure and/or chemical composition, and one or more of them may comprise the sensate.

In some embodiments, the cartridge comprises a guard comprising at least one elongated flexible protrusion to engage a user's skin. The at least one flexible protrusion may comprise flexible fins generally parallel to said one or more elongated edges (hair removal members). Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695A1 (disclosing an elastomeric guard having guard forming at least one passage extending between an upper surface and a lower surface). In some embodiments, said shaving aid member is positioned on the cartridge aft of the guard and forward of the hair removal members. In another embodiment, the shaving aid member is positioned on the cartridge forward of the guard. This embodiment can be particularly useful to deliver the lubricating material prior to contact with the guard.

VII. Hair Removal Device

According to some embodiments of the invention, a hair removal device (e.g. a razor) is provided, which generally comprises a hair removal cartridge (e.g. a razor cartridge) according to the invention as described hereinabove, and a handle (or grip portion) permanently or removably attached to the cartridge. The hair removal device can be manual or power driven and can be used for wet and/or dry application. The hair removal cartridge may be replaceable and/or pivotally connected to the handle (e.g. via a cartridge connecting structure) and in turn or independently (e.g. permanently fixed) to a handle. In some embodiments, the cartridge connecting structure includes at least one arm to releasably engage the hair removal cartridge.

VIII. Method of Making

Any of the shaving aid members of the present invention may be fabricated by any appropriate method, including injection molding, pressing, impregnation, spray-coating, calendaring and extrusion, the latter being preferred. All of the components of the strip can be blended prior to molding or extrusion. For best results, it is preferred that the components are dry. In summary, the method comprises the steps of providing a feed comprising a water soluble polymer having an average molecular weight of at least 5000; and a copolymer of polyethylene oxide and polypropylene oxide; preferably heating said feed to a temperature of from 120° C. to 200° C., and molding, pressing, impregnating, spray-coating, calendaring and/or extruding said feed to form a shaving aid member.

For example, the blended components may be extruded through a Haake System 90, ¾ inch diameter extruder with a barrel pressure of about 1000-2000 psi, a rotor speed of about 10 to 50 rpm, and a temperature of about 150°-185° C. and a die temperature of about 170°-185° C. Alternatively, a 1¼ inch single screw extruder may be employed with a processing temperature of 175°-200° C., preferably 185°-190° C., a screw speed of 20 to 50 rpm, preferably 25 to 35 rpm, and an extrusion pressure of 1800 to 5000 psi, preferably 2000 to 3500 psi. The extruded strip is air cooled to about 25° C. To injection mold the strips it is preferred to first extrude the powder blend into pellets. This can be done on a 1¼ or 1½ inch single screw extruder at a temperature of 120°-180° C., preferably 140°-150° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 165° to 250° C., preferably from 180° to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

IX. Details on Figures

Figure 2:
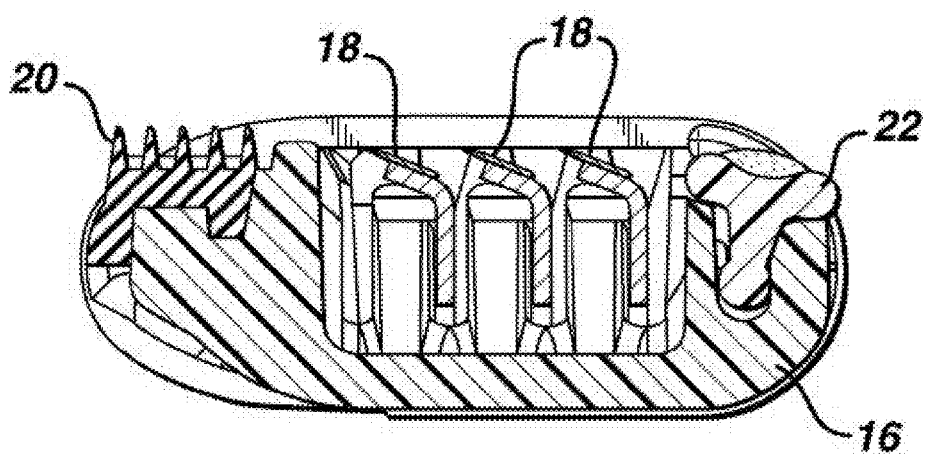
FIG. 2 is a sectional view taken along line 2-2 of FIG. 1.
Figure 3:
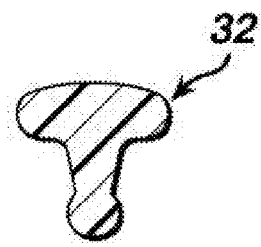
FIG. 3 is a side elevation view of a second type of shaving aid member of the present invention.

Referring to FIGS. 1 and 2, the razor cartridge 14 includes housing 16, which carries three blades 18, a finned elastomeric guard 20, and a shaving aid member 22 located on a skin-engaging portion (in this case the cap) of the cartridge. Shaving aid member 22 is shown having two layers, the first layer can be according to the present invention, and the second layer can be a conventional shave aid, or vice versa. The shaving aid member is preferably locked in (e.g. via adhesive, a fitment, or melt bonding) an opening in the rear of the cartridge. Shaving aid member 32, shown in FIG. 3, is similar to shaving aid member 22, except that shaving aid member 32 has a homogeneous composition throughout and a uniform, slightly curved to flat upper surface. Shaving aid members according to the invention may also be fabricated in a wedge-shaped cross-section or any other desired shape. The shaving aid member may also be constructed in two or more layers, such as a sandwich or a sheath/core construction.

X. Methods of Hair Removal (Especially Shaving)

The hair removal cartridge (especially a razor cartridge) or hair removal device (especially a razor) of the present invention may be used for hair removal (especially shaving), or in a method of hair removal (especially shaving), the method comprising the steps of providing a hair removal cartridge (especially a razor cartridge) or hair removal device (especially a razor) according to the present invention in any form, and passing the same over a surface of the body. Optional additional steps may include wetting the surface, washing the surface, applying one of various commonly known shaving preparations to the surface, (the preceding options typically occurring before passing the hair removal/razor cartridge or hair removal device/razor over the surface), rinsing the surface (which could occur prior to and/or after passing the hair removal/razor cartridge or hair removal device/razor over the surface), drying the surface and applying one of various commonly known post-shave compositions to the surface (the last two steps typically occurring after passing the hair removal/razor cartridge or hair removal device/razor over the surface)

XI. Examples

The following examples can be made according to the below tables with the following method: ingredients are blended and mixed with other ingredients in a tumbler to make a homogeneous powder. The obtained powder is then single extruded into shaving aid members at 160-180° C. and 100-200 bar pressure.

| Ingredient | Comparative Example | Inventive Example 1 | Inventive Example 2 |
|---|---|---|---|
| Polyox Coagulant (PEO)* | 34.86 | 32.36 | 29.86 |
| Polyox WSR N750 (PEO)** | 24.39 | 21.89 | 19.39 |
| Carbowax 4600 (PEG, mol. wt = 4600) | 5.00 | 5.00 | 5.00 |
| ECM HIPS 5410*** | 26.50 | 26.50 | 26.50 |
| Capa 6506S (Polycaprolactone) | 5.00 | 5.00 | 5.00 |
| Green Colorant | 4.00 | 4.00 | 4.00 |
| B215 Irganox (antioxidant) | 0.25 | 0.25 | 0.25 |
| Pluronic F127 (PEO-PPO Copolymer) | 0.00 | 5.00 | 10.00 |
| Total | 100.00 | 100.00 | 100.00 |

*Average molecular weight of 5,000,000
**Average molecular weight of 300,000
***High impact polystyrene The coefficient of friction of a common razor cartridge (consistent design between measurements) bearing each of the example shaving aid members (physically identical) above was measured against a polyurethane skin mimic having dimensions of 3 inches (7.5 cm) by 6.5 inches (17 cm) on a Dia-stron MTT175 instrument fitted with a 2000 g/cm$^2$ horizontal load cell. The skin mimic was warmed to a temperature of 27° C., and a downward force of 300 g (equivalent as mass) applied. The razor cartridge (including the shaving aid member) was soaked in water at a temperature of 55° C. and 1 ml of water (also warmed to 55° C.) was applied to the skin mimic to wet it prior to measurement. The UvWin software package supplied with the Dia-stron instrument (v.1.24.0000) was used to run three overlapping, subsequent 100 mm long strokes with the razor cartridge at a speed of 1500 mm/min, ensuring that the razor cartridge did not contact the skin mimic when moving between strokes. Following the three strokes, the skin mimic was removed from the apparatus to be washed with hot water, scrubbed clean by hand, wiped with a paper towel and re-rinsed before being replaced on the apparatus ready for the next sample. The coefficient of friction was calculated for each stroke based upon the middle 70 mm length of the stroke (i.e. from 15 mm along the stroke to 85 mm along the stroke).

Figure 4:
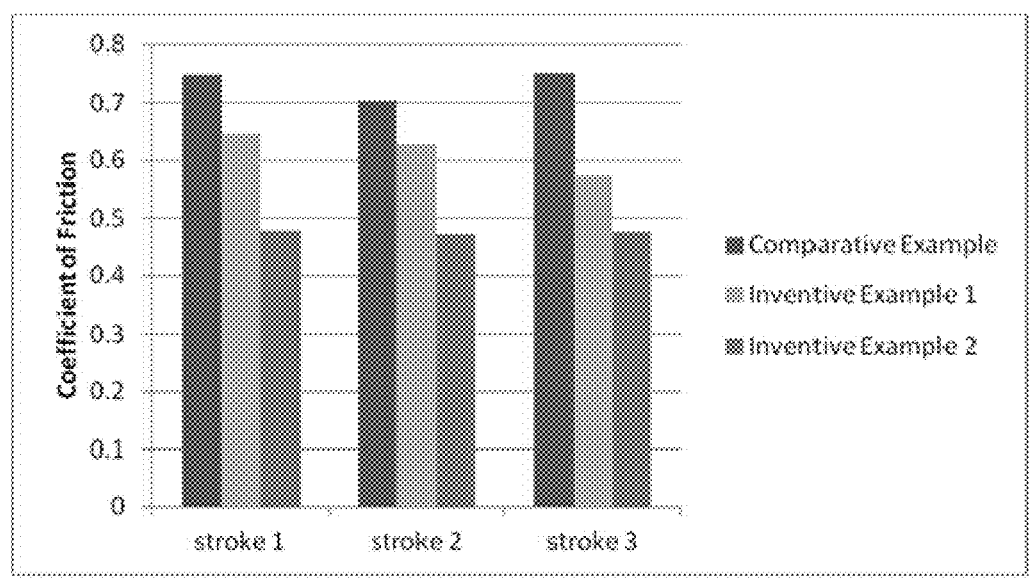
FIG. 4 is a chart showing coefficient of friction results for comparative examples.

This procedure was repeated to yield results from a total of 5 shaving aid members for each example. The results for each of the three strokes (averages of the 5 shaving aid members) appear in the graph shown in FIG. 4. The data shown in FIG. 4 clearly shows that the addition of the copolymer of polyethylene oxide and polypropylene oxide reduces the coefficient of friction afforded by the examples tested.

As used herein, molecular weights (mol.wt.s) are provided in unified atomic mass units, daltons, or g/mol.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. Similarly, it should be understood that each feature of the each specified embodiment of the invention may be independently applied to each other specified embodiment, as if all such combinations were expressly written herein, unless these combinations are specifically excluded or the relevant features are innately incompatible (e.g. the features are directly contradictory).

All parts, ratios, and percentages herein, in the Description, Examples, and Claims, are by weight of the shaving aid member and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern. Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the spirit and scope of this invention.

What is claimed is:

1. A shaving aid member comprising a lubricating material, the lubricating material comprising:
   a. about 50% or more, by weight of the lubricating material, of a water soluble polymer having an average molecular weight of from about 100,000 to about 6,000,000, wherein said water soluble polymer comprises
      i. a first polyethylene oxide having an average molecular weight of 300,000 in an amount of 29% to 32%, by weight of the lubricating material, and
      ii. a second polyethylene oxide having an average molecular weight of 5,000,000 in an amount of from 19% to 22%, by weight of the lubricating material; and
   b. from about 5% to about 10%, by weight of the lubricating material, of a copolymer of polyethylene oxide and polypropylene oxide, wherein the copolymer of polyethylene oxide and polypropylene oxide has an average molecular weight of from 12,000 to 13,000.

2. The shaving aid member of claim 1, wherein the copolymer of polyethylene oxide and polypropylene oxide is a block copolymer.

3. The shaving aid member of claim 1, wherein the ratio of polyethylene oxide to polypropylene oxide in the copolymer of polyethylene oxide and polypropylene oxide is in the range of from about 10:1 to about 1:10.

4. The shaving aid member of claim 1, wherein the water soluble polymer is selected from polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and mixtures thereof.

5. The shaving aid member of claim 1, wherein the water soluble polymer is polyethylene oxide.

6. The shaving aid member of claim 1, wherein the water soluble polymer has an average molecular weight from about 300,000 to about 5 million.

7. The shaving aid member of claim 1, wherein the water soluble polymer is present at a level from about 70% to about 90% by weight of the lubricating material.

8. The shaving aid member of claim 1, wherein the shaving aid member further comprises a water insoluble polymer, and wherein the lubricating material is dispersed within the water insoluble polymer.

9. The shaving aid member of claim 8, wherein the water insoluble polymer is selected from: polyethylene, polypropylene, polystyrene, high impact polystyrene, butadiene styrene copolymer, polyacetal, acrylonitrile-butadiene styrene copolymer, ethylene vinyl acetate copolymer, and mixtures thereof.

10. The shaving aid member of claim 8, wherein the water insoluble polymer is present at a level of from about 15% to about 35% by weight of the shaving aid member.

* * * * *